United States Patent [19]

Long

[11] 4,090,752

[45] May 23, 1978

[54] DIAGNOSTIC ELECTRODE ASSEMBLY

[75] Inventor: Gregor Dean Long, Libertyville, Ill.

[73] Assignee: Baxter Travenol Laboratories, Inc., Deerfield, Ill.

[21] Appl. No.: 745,684

[22] Filed: Nov. 29, 1976

Related U.S. Application Data

[62] Division of Ser. No. 512,589, Oct. 7, 1974, abandoned.

[51] Int. Cl.² .............................................. A61B 5/04
[52] U.S. Cl. ...................................... 312/42; 312/50; 128/2.06 E
[58] Field of Search ..................... 312/42, 45, 46, 49, 312/50, 60, 71, 72; 128/2.06 E, 2.1 E, 417

[56] References Cited

U.S. PATENT DOCUMENTS

| 1,627,870 | 5/1927 | Seidemann | 312/45 |
| 3,316,040 | 4/1967 | McGann | 312/45 |
| 3,834,373 | 9/1974 | Sato | 128/2.06 E |

FOREIGN PATENT DOCUMENTS

| 296,835 | 9/1928 | United Kingdom | 312/49 |

Primary Examiner—Casmir A. Nunberg
Attorney, Agent, or Firm—Paul C. Flattery; John P. Kirby, Jr.; Gary W. McFarron

[57] ABSTRACT

A disposable electrode assembly for establishing electrical contact with an underlying skin surface includes a relatively thin transparent base member having a central hub portion and an adhesive-coated undersurface, a conductive gel-impregnated sponge contact contained in a downwardly facing recess located in the hub, and a relatively thick and inflexible cover member coextensive with the base member. In storage the cover member is attached to the undersurface of the base member by the adhesive and the sponge is confined within the recess. Prior to use the base member is peeled away from the cover member to expose the adhesive surface, which when applied to a skin surface holds the sponge contact in compression-contact therewith. The base is transparent to enable the user to detect skin irritation and incomplete adhesion of the base member, and may be provided with apertures to facilitate breathing of the underlying skin. A combined container and dispenser for conveniently storing and dispensing the electrode assemblies is shown.

7 Claims, 12 Drawing Figures

U. S. Patent    May 23, 1978    Sheet 1 of 3    4,090,752
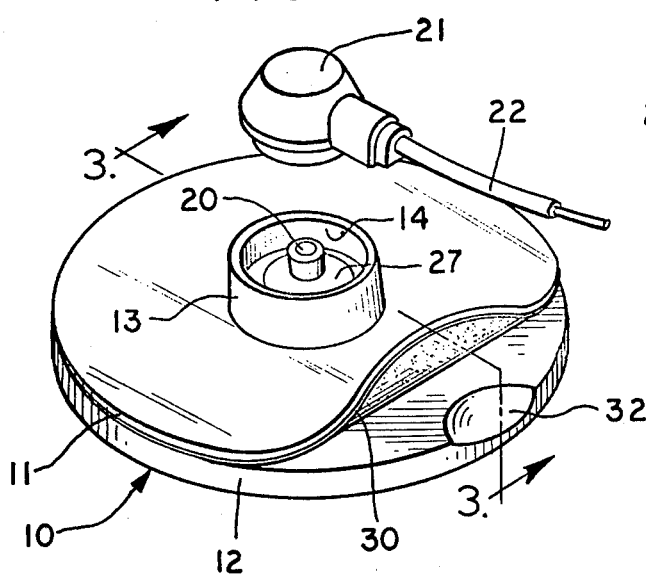
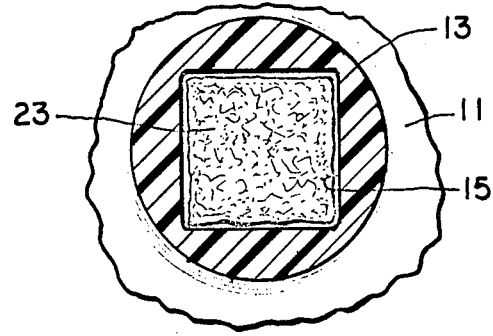
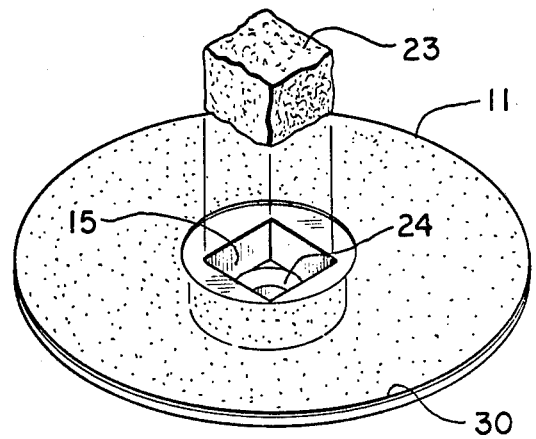
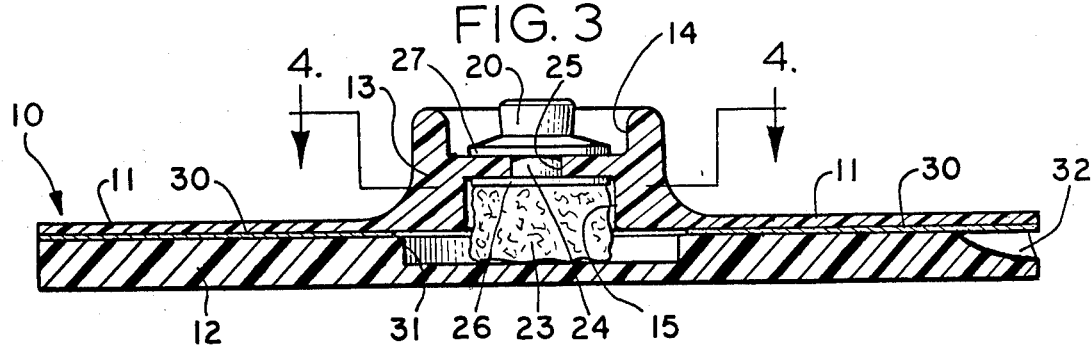
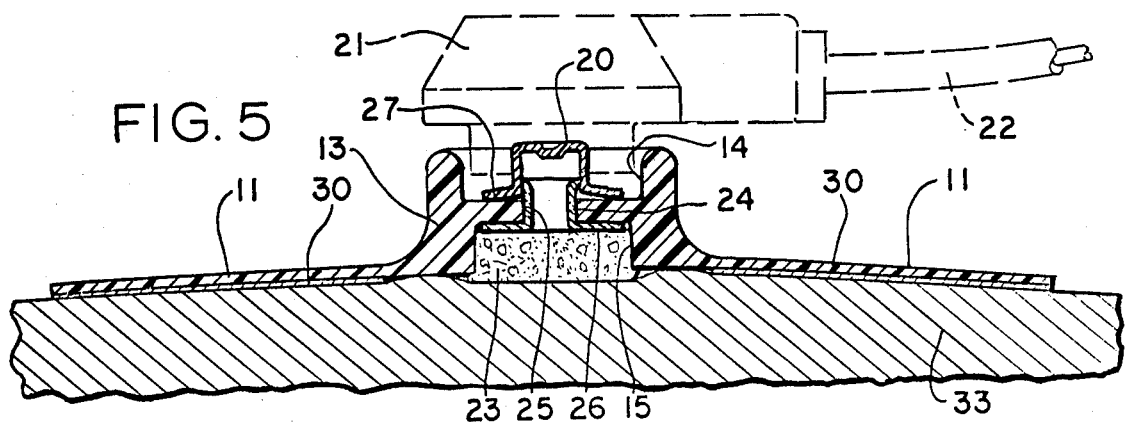

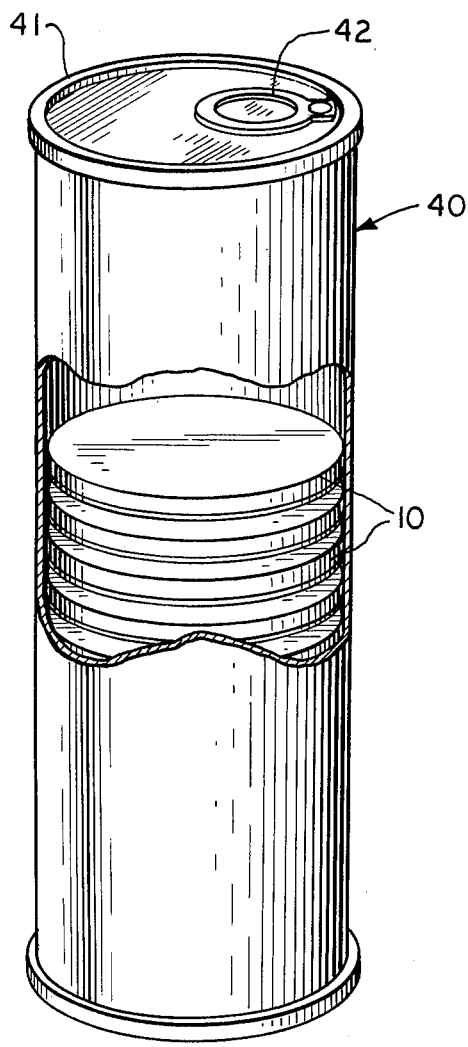
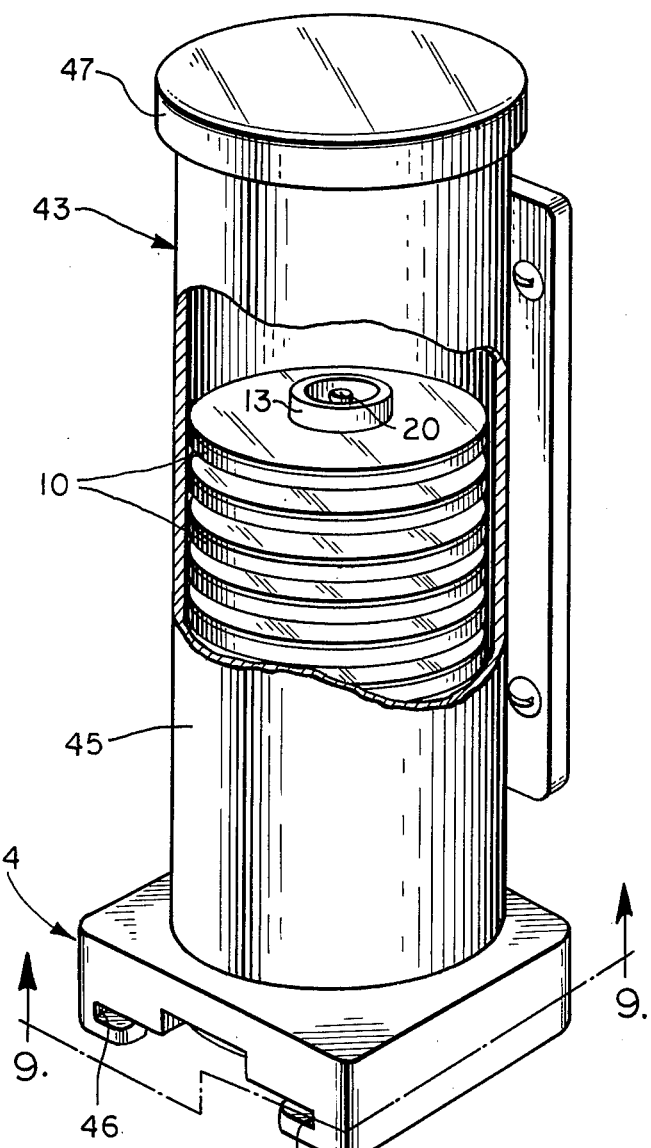
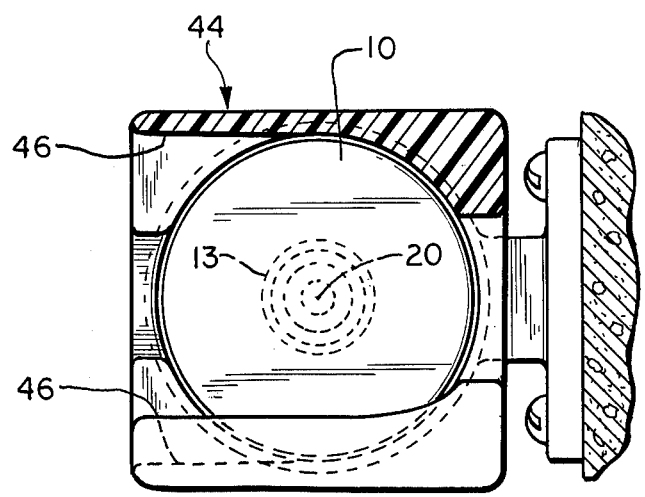

DIAGNOSTIC ELECTRODE ASSEMBLY

This is a division, of application Ser. No. 512,589, filed Oct. 7, 1974 now abandoned.

BACKGROUND OF THE INVENTION

The present invention relates generally to disposable electrodes, and more particularly to a skin contact electrode assembly for detecting cardiac and other low level electrical signals generated within the human body.

Skin contact electrodes find extensive use for detecting and transforming potentials generated within the body into electrical signals which may be monitored for a variety of functions, such as the preparation of electrocardiograms and electroencephalograms. Originally, such electrodes were of the permanent or non-disposable type wherein a metal electrode was placed in contact with the skin with an interposed layer of electrolyte, generally in gel form. Not only was the placing of the electrode, which often had to be strapped to the patient, cumbersome and inconvenient, but the application of the gel electrolyte had to be done very carefully to avoid contact with the clothes of the patient and the person conducting the test. In addition, the electrodes had to be cleaned after each use for reasons of sanitation and to insure a good electrical contact.

In recent years, with the advent of portable and more sophisticated EKG and other types of biomedical monitoring equipment, disposable electrode assemblies, wherein the metallic electrode and the electrolyte gel, together with an adhesive for holding the electrode in position, are combined in a unitary assembly for one-time use, have come into wide use. Not only do these assemblies avoid the time-consuming processes of applying gel and strapping the electrode in position, but they also avoid the necessity of cleaning the electrode after each use.

Unfortunately, prior art disposable type electrode assemblies have not been entirely satisfactory in all respects. Typically, such electrode assemblies have used thin paper or plastic adhesive-backed base members to which the electrode was attached, and a cover member for covering the adhesive until ready for use. Because the base and cover members provided little or no stiffness to the assemblies, the assemblies were difficult to store and difficult to prepare for use. Furthermore, the elements of the assembly were often torn or damaged in attempting to remove the cover member prior to use, and the user was often subjected to undesired contact with either the electrolyte gel or the adhesive.

The lack of stiffness in prior art electrode assemblies also precluded stacking of the assemblies while in storage, making it necessary to package each assembly in an individually sealed package suitable for storage in a drawer or open box. This not only unnecessarily consumed the time of the user by requiring him to unwrap each package separately prior to use, but also unnecessarily increased the cost of the electrode assemblies. Attempts at placing more than one electrode assembly in a package proved unsatisfactory because the number of electrodes required for a particular situation varied, resulting in the unwrapping and discarding of unneeded electrodes. Accordingly, the need has developed for a disposable electrode assembly which can be conveniently stored and dispensed in a desired quantity with no waste or damage to unused electrodes.

Those assemblies which utilized a thicker or stiffer base member in attempting to overcome these deficiencies tended to separate from the skin after a period of time, and often caused discomfort to the patient during extended monitoring periods. Use of a stronger adhesive to hold the stiffer base members in position aggravated the discomfort of the patient as the electrodes were removed or repositioned. The use of a stiffer base member in prior art electrode assemblies also increased the possibility of spurious output signals being produced as the patient moved. Such motion artifacts resulted from mechanical disturbance of the electrolyte relative to the metal electrode, which was aggravated by the use of a stiff base member above the skin contact area.

Occasionally skin contact electrodes are utilized in a continuing monitoring process where it is necessary to leave the electrodes in position over an extended period of time, for days or even weeks. In this situation, it is desirable to periodically monitor the condition of the patient's skin under the electrode assembly for possible irritation. With prior art electrode assemblies it was necessary to periodically peel the assembly at least partially away from the skin for this purpose, thereby increasing the likelihood of the skin becoming irritated and the adhesion capabilities of the adhesive being weakened. Thus, the need exists for a disposable electrode assembly which allows skin condition to be monitored without disturbing the electrode.

In addition to the aforementioned attributes of convenience of storage and use, it is necessary that a body electrode assembly of the disposable type be economical to manufacture and package. To this end the materials employed in its manufacture must be readily obtainable and the individual components utilized in the assembly must be capable of fabrication by efficient techniques and processes. It is to a new and improved disposable electrode assembly which combines the desired economy of construction and convenience of packaging with low contact resistance, good adhesion and low motion artifacts, that the present invention is directed.

SUMMARY OF THE INVENTION

The invention is directed to a disposable electrode assembly for establishing and electrical connection to an underlying skin surface. The electrode assembly comprises a base member formed at least partially of transparent electricallyinsulating material having an outside surface and an inside surface, means including an electrically conductive terminal having a first portion on the outside surface and a second portion on the inside surface for establishing electrical contact with the skin surface, and means including a transparent adhesive layer on the inside surface of the base member for attaching the base member to the underlying skin surface, the skin surface being viewable through the base member and adhesive layer.

The invention is further directed to a container assembly for storing disposable body electrode assemblies of the type having base and cover members joined during storage by an interposed layer of adhesive and forming a relatively stiff peelably separable assembly. The container comprises a housing forming an elongated chamber for receiving a plurality of the electrode assemblies in stacked relationship, the chamber having a uniform inside cross-section along its length complementary to the outside dimension of the electrode assemblies, and means comprising a pair of cover members at respective ends of the housing for sealing the chamber, at least one of the cover members being user-removable to gain access to the electrode assemblies.

The invention is further directed to a dispenser for dispensing disposable body electrode assemblies of the type having base and cover members joined during storage by an interposed layer of adhesive and forming a relatively thin stiff peelably separable assembly. The dispenser comprises a housing forming an elongated chamber for receiving a plurality of the electrode assemblies in stacked relationship, the chamber having a uniform inside cross-section along its length complementary to the outside dimension of the electrode assemblies, mounting means for supporting the housing in a substantially vertical upstanding relationship whereby the electrode assemblies are contained in the chamber in a substantially vertical relationship, and means comprising a dispensing station at the bottom end of the housing for enabling a user to remove the body electrodes one at a time from the chamber.

BRIEF DESCRIPTION OF THE DRAWINGS

The features of the present invention, which are believed to be novel, are set forth with particularity in the appended claims. The invention, together with the further objects and advantages thereof, may best be understood by reference to the following description taken in connection with the accompanying drawings, in the several figures of which like reference numerals identify like elements, in which:

FIG. 1 is a perspective view of an electrode assembly constucted in accordance with the invention showing the base member partially peeled away from the backing member and showing a mating electrical contact for establishing electrical contact with the assembly.

FIG. 2 is a perspective view of the electrode assembly inverted showing the sponge-like skin contact member of the assembly removed from its recess in the inside face of the transparent base element of the assembly.

FIG. 3 is a cross-sectional view taken along lines 3—3 of FIG. 1 showing the cover element of the electrode assembly in position for storage.

FIG. 4 is an enlarged cross-sectional view taken along lines 4—4 of FIG. 3 showing the raised or hub portion of the base member of the assembly.

FIG. 5 is a cross-sectional view of the electrode assembly showing the assembly in position on an underlying skin surface with a mating electrical connector shown in phantom.

FIG. 7 is a perspective view, partially broken away to show the interior, of a storage container for the electrode assemblies.

FIG. 8 is a perspective view, partially broken away to show the interior, of a vertical dispenser for the electrode assemblies.

FIG. 9 is a cross-sectional view of the dispenser of FIG. 8 taken along lines 9—9 of FIG. 8.

DESCRIPTION OF THE PREFERRED EMBODIMENT

Figure 6:
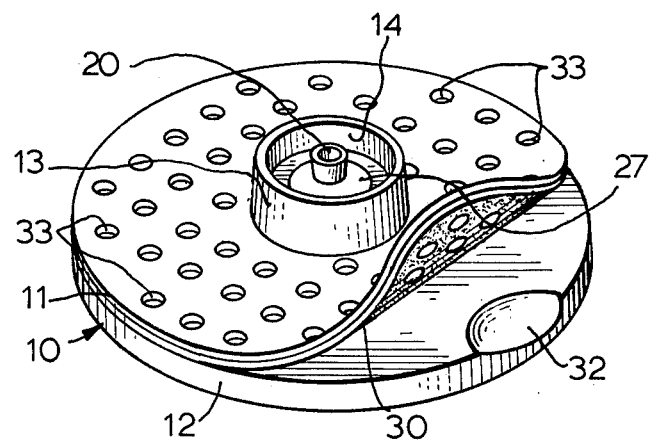
FIG. 6 is a perspective view of an electrode assembly constructed in accordance with the invention, wherein the base member has been provided with a plurality of apertures to facilitate breathing of the underlying skin surface.

Referring to the figures, and particularly to FIGS. 1–3, an electrode assembly 10 incorporating the features of the present invention is seen to comprise a relatively thin flexible disc-shaped base member 11 formed or molded of a transparent non-conducting material such as plastic, and a relatively thick and inflexible disc-shaped cover member 12 of like diameter formed or molded of an opaque plastic material. The top (FIG. 1) or outside surface of the base includes a central raised or hub portion 13 which includes an upwardly facing open-ended recess or chamber 14, and the bottom or inside surface of the base includes a four-sided downwardly-facing open-ended recess or chamber 15.

To facilitate electrical connection to an associated monitoring apparatus, an electrical snap-type connector terminal 20 is provided within chamber 14. This terminal, which may be of conventional design and construction, includes a slightly tapered upwardly extending cylindrical portion which engages complementarily dimensioned inwardly-biased downwardly-extending contact fingers (not shown) on a female connector 21, which also may be conventional in design and construction. The effect of the open-ended chamber 14 is to form a socket or wall around terminal 20 which helps to prevent inadvertent disengagement of connector 21 from terminal 20, and inadvertent contact by the user with the electrical circuit established through the connector and the consequent erroneous output signals which might result from such contact. Connector 21 is connected by an insulated conductor 22 of an appropriate length to the monitoring apparatus.

Electrical contact is made to the patient's skin by means of a compressible body contact member 23, which may be fabricated from a sponge-like material impregnated with an electrically conductive gel. While contact member 23 can be formed in various shapes and dimensions, it is preferably sized to fit within and occupy substantially the entire inside volume of chamber 15 to achieve the largest possible skin contact area for the lowest possible contact resistance. To this same end, the vertical dimension (in FIGS. 3 and 5) of contact member 23 is preferably such that the contact member is under compression when the inside surface of base 11 is pressed against the skin surface, as shown in FIG. 5.

An electrical connection is established between body contact member 23 and terminal 20 by means of a rivet-shaped electrically conductive retaining member 24 which extends between the rear wall of chamber 15 and the bottom of terminal 20. The retaining member 24 extends through an aperture 25 provided in base 11 between chamber 15 and chamber 14, and into a locking press-fit engagement with terminal 20. A flange portion 26 at the bottom end (as viewed in FIGS. 3 and 5) of member 24 prevents the member from being pulled through aperture 25 and provides increased contact area for establishing a low resistance electrical connection with body contact member 23. A similar flange portion 27 on contact 20 prevents that member from being pulled through aperture 25, so that once members 20 and 24 have been press-fit together during manufacture of the electrode assembly a very secure electrically-integral attachment between the contacts and base 11 is obtained.

Referring to FIG. 3, while being stored prior to use the disc-shaped cover plate 12 overlies the interior surface of base 11 and is attached thereto by means of an adhesive layer 30, which preferably comprises an acrylic-based adhesive of a type which does not promote allergic reactions or irritations to the skin. This adhesive is deposited on both sides of a thin transparent disc-shaped polyethylene carrier or barrier which is provided with a central aperture so as not to overlie the open end of chamber 15. The adhesive layer is sandwiched between the interior surface of base 11 and cover 12 to hold the two elements together and cover member 12 is preferably provided with an open-ended chamber or recess 31 on its inside surface to allow partial expansion of the sponge-like skin contact 23 during storage. This enables the sponge to retain a greater quantity of conductive gel during storage, and consequently to release a greater amount of gel onto the underlying skin surface when compressed prior to use.

Prior to applying the electrode assembly 10 to a skin surface, the thin flexible and transparent base member 11 is peeled away from the relatively stiff cover member 12 to expose the adhesive surface, as shown in FIG. 1. To facilitate removal of the cover member a thumb recess 32 may be provided along the circumferential margin of cover 12. Since the cover is formed of thicker and less flexible material than the base 11, peeling the base member away from the backing member can be readily accomplished once the cover is initially separated by means of recess 32.

After the cover 12 has been removed the electrode assembly can be applied by pressing the inside surface of the base member 11 to the skin surface 33, as shown in FIG. 5. This compresses the sponge-like skin contact member 23 and releases conductive gel onto the underlying skin area, thereby establishing a low-resistance electrical connection through member 23 to the skin surface. The adhesive layer 30, which is substantially coextensive with the interior surface of base 11, adheres to the skin to hold the electrode assembly in position. To accomplish this the area of the adhesive 30 on the interior surface of base 11, and hence the diameter of the base, must be sufficiently large to obtain and adequate adhesive force, taking into consideration that the adherence of the adhesive to the skin must not be so great as to cause unnecessary discomfort to the patient when the electrode assembly is removed.

In a preferred embodiment of the invention the base member 11 is preferably fabricated of a transparent flexible polymer plastic or a suitable rubber-like material. One material which has proven successful for this application is polyvinyl chloride. In one exemplary embodiment the base member 11 may have an overall diameter of 2.5 inches, a skirt thickness of 0.021 inch, and a recess of 0.125 inch depth and 0.46 inch diameter.

Referring to FIG. 6, it is contemplated that the base member may be provided with a plurality of apertures 33 to allow the skin beneath the cover element to breathe, thereby lessening the likelihood of skin irritation when the electrode assembly is left in position for an extended period of time. Although it is contemplated that these apertures may have various shapes and dimensions, and may be provided on the surface of base 11 in various densities, in a preferred embodiment the apertures 33 have a diameter of 1/64 inch and a density of 16 apertures per square inch of surface area. The transparency of the base member 11 is also beneficial in this instance, since it allows the underlying skin surface to be periodically checked for irritation without disturbing the electrode, and allows the operator of the monitoring equipment to detect and eliminate areas under the base where the adhesive is not in contact with the skin.

The cover member 12 may be formed of a hydrophilic material such as polyethylene and may have color added to color code the electrode during storage. Typically, cover member 12 may have a thickness of approximately 0.125 inch except under recess 31 wherein it may have a typical thickness of approximately 0.05 inch. In the exemplary embodiment the cover member preferably has a diameter of 2.532 inches and a recess having a diameter of 0.687 inch and depth of 0.075 inch. The sponge-like skin contact member 23 may be formed of a polyether polyurethane foam impregnated with an ionic fluid in a suitable organic based gel, for example, that currently available from Parker Laboratories, Inc. under the trademark Spectra 360 or that available from Pharmaceutical Innovations, Inc. under the trademark LECTRON II, although other conductive fluids or gels may be used without departing from at least the broader principles of the present invention.

To reduce the attraction between the gel-impregnated contact member 23 and the cover 12 as the base 11 is peeled away, the base is preferably formed of a material which is more hydrophilic than the cover. This is believed to cause the gel-impregnated sponge to be attracted to the base to a greater extent than it is attracted to the cover, and therefore to tend to remain with the base. The snap terminal 20 and retaining member 24 are preferably formed of silver, silver-coated brass, brass, rhodium-coated brass, nickel, zinc-coated brass, or stainless steel, although other conductors may be employed. Silver is preferred because it has the lowest half cell potential and therefore generates the least spurious signal with relative motion of contacts 20 and 21 as the patient moves.

By reason of its unique construction the electrode assembly of the present invention lends itself to packaging concepts which provide more convenient dispensing and longterm storage. Referring to FIG. 7, the electrode assemblies can be stored for long periods of time in a sealed cylindrical container 40. This container may be provided with a removable air-tight end cover 41 on one end of a type which can be conveniently removed by pulling a pull ring 42 attached to the outer surface thereof prior to using the first electrode assembly in the package. Once opened, the unused electrode assemblies in the container remain stacked one on top of the other for optimum utilization of available storage space. Since the container is sealed prior to the top cover being removed, the assemblies within are protected from deterioration for extended periods of time. Once the container has been opened, cover 12 serves to protect the adhesive 30 and gel-impregnated contact member 23 from direct contact with the air and consequent deterioration during the remaining storage period prior to their eventual use.

Referring to FIGS. 8 and 9, the disposable electrode assemblies can also be stacked, one on top of the other, in a vertical dispenser 43 for delivery one at a time at an underlying dispensing station 44. The electrode assemblies 10 are arranged contact-up in a cylindrical housing 45 so as to fall into position behind a dispensing slot 46 as the next adjacent underlying electrode assembly is removed for use. In this way, the number of electrode assemblies needed for a particular monitoring function can be removed while those not required remain in an orderly stacked arrangement. As the supply of assemblies in the dispenser becomes depleted, additional assemblies can be added from the top end of housing 45 by removing an end cover 47, which may be pressfit into position in the top end of housing 45 for convenient access to the interior of the housing.

Figure 10:
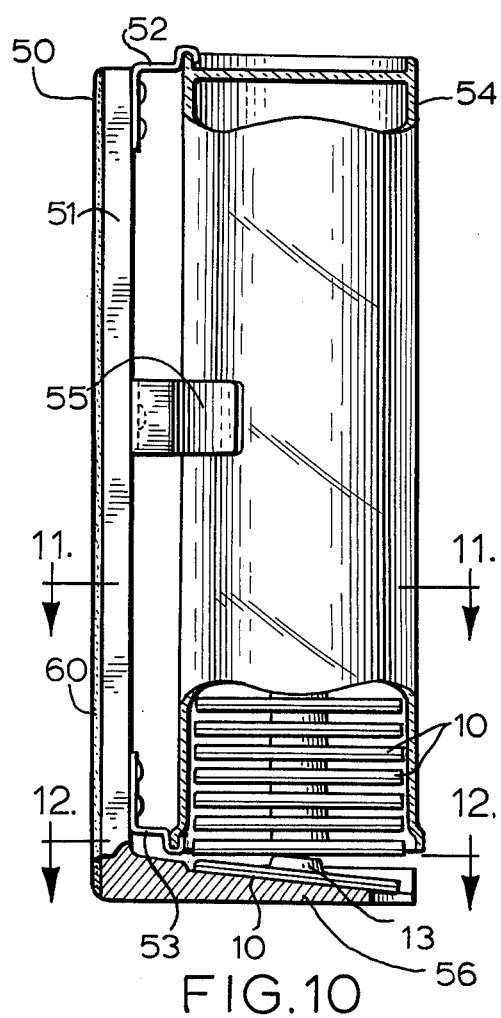
FIG. 10 is a perspective view, partially broken away to show the interior, of an alternate vertical dispenser for the electrode assemblies.
Figure 11:
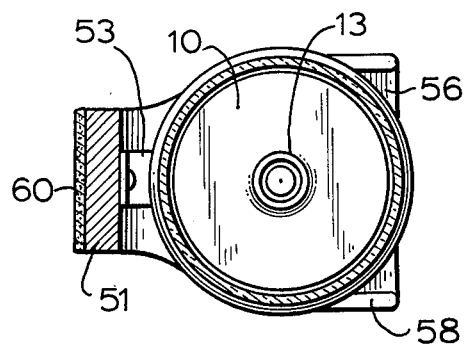
FIG. 11 is a cross-sectional view of the dispenser of FIG. 10 taken along lines 11—11 of FIG. 10.
Figure 12:
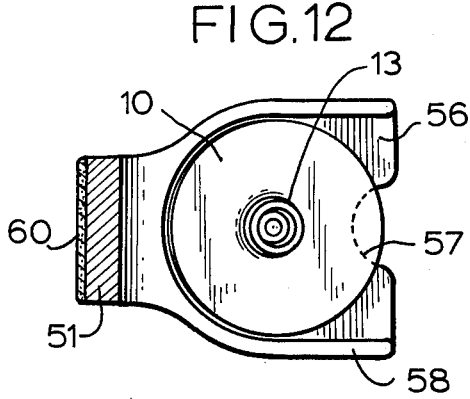
FIG. 12 is a cross-sectional view of the dispenser of FIG. 10 taken along lines 12—12 of FIG. 10.

An alternative form of vertical dispenser 50 is shown in FIGS. 10–12. This dispenser includes a vertical frame 51 provided with top and bottom spring retaining clips 52 and 53 appropriately spaced to engage the top and bottom edges of a hollow cylindrical container 54 within which a quantity of electrodes 10 are stacked, one on top of the other, contact up. The bottom edge of the container 54 may be provided with an outwardly extending flange to receive clip 53 as shown in FIG. 10, or alternatively may be provided with no flange where sufficient clearance exists between the electrode assemblies 10 and the inside of the container 54 so that the clip does not interfere with the gravity feed of the electrode assemblies. By deforming one or the other of the spring clips, the container can be removed for replacement or reloading. A wing-shaped clip or bracket 55 may be provided on frame 51 between clips 52 and 53 to aid in holding container 54 in alignment.

The bottom end of frame member 51 extends forwardly to form a shelf portion 56 on which the electrode to be next dispensed is positioned. As can be seen in FIG. 10, this shelf portion 56 is preferably slightly downwardly inclined to separate the leading edge of the next to be dispensed electrode for the leading edges of the stacked electrodes above so that the user can readily grasp the electrode prior to pulling it forwardly from the dispenser. As shown in FIG. 12, the shelf portion 56 may also be provided with a notch 57 along its front edge to facilitate grasping the leading edge of the bottom electrode, and a peripheral ledge 58 to assist in holding the bottom electrode in alignment. It is contemplated that the dispenser may be mounted to a vertical surface such as a wall or cabinet by means of a layer 60 of adhesive on the rear surface of frame 51, or by means of a plurality of screws or other fastening devices (not shown) extending through the frame and into the supporting surface.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

I claim:

1. A dispenser for dispensing disposable body electrode assemblies of the type having disc-shaped base and cover members joined during storage by an interposed layer of adhesive and forming a relatively thin stiff peelably separable assembly, said dispenser comprising, in combination:

a housing forming an elongated chamber for receiving a plurality of said electrode assemblies in stacked relationship, said chamber having a uniform inside cross-section along its length complementary to the outside dimension of said electrode assemblies;

mounting means for supporting said housing in a substantially vertical upstanding relationship whereby said electrode assemblies are contained in said chamber in a substantially vertical stacked relationship;

means comprising a dispensing station at the bottom end of said housing for enabling a user to remove said body electrodes one at a time from said chamber;

said dispensing station includes a bottom passageway to pass a single one of said disc-shaped body electrodes at one time; and said passageway is closed throughout opposing peripheral extents thereof.

2. A dispenser as defined in claim 1 wherein said bottom passageway is a slot arranged in a plane at right angles to the axis of said chamber.

3. A dispenser as defined in claim 1 which includes means for mounting said housing with the axis of said chamber substantially vertical whereby as the bottom electrode assembly in said chamber is removed through said slot the next adjacent electrode assembly stacked thereabove falls into position behind said slot.

4. A container assembly as defined in claim 3 wherein said chamber is cylindrical.

5. A dispenser as defined in claim 1 wherein said bottom end of said container is open, and said bottom passageway comprises a shelf underlying said bottom end of said container, said shelf being dimensioned to receive the bottom one of said stacked electrode assemblies.

6. A dispenser as defined in claim 5 wherein said shelf is inclined slightly downwardly with respect to the axis of said housing to separate at least a portion of the edge of the bottom one of said stacked electrode assemblies from the next adjacent electrode assembly above.

7. A dispenser as defined in claim 6 wherein said shelf includes a ledge adjacent at least a portion of its periphery to index said bottom electrode for convenient removal by a user.

* * * * *